(12) United States Patent
Dohmen et al.

(10) Patent No.: US 11,389,251 B2
(45) Date of Patent: *Jul. 19, 2022

(54) METHOD FOR REGISTERING ARTICULATED ANATOMICAL STRUCTURES

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Lars Dohmen, Munich (DE); Mario Schubert, Poing (DE); Anna Wiedenmann, Feldkirchen (DE)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 175 days.

This patent is subject to a terminal disclaimer.

(21) Appl. No.: 16/845,630

(22) Filed: Apr. 10, 2020

(65) Prior Publication Data
US 2020/0237447 A1 Jul. 30, 2020

Related U.S. Application Data

(63) Continuation of application No. 15/576,172, filed as application No. PCT/EP2015/062008 on May 29, 2015, now abandoned.

(51) Int. Cl.
*A61B 34/20* (2016.01)
*G06T 7/73* (2017.01)
(Continued)

(52) U.S. Cl.
CPC .............. *A61B 34/20* (2016.02); *A61B 34/10* (2016.02); *G06T 7/32* (2017.01); *G06T 7/337* (2017.01);
(Continued)

(58) Field of Classification Search
CPC .............. A61B 34/10; A61B 2034/105; A61B 2090/376; A61B 2090/364; A61B 5/1121;
(Continued)

(56) References Cited

U.S. PATENT DOCUMENTS 8,675,939 B2 3/2014 Moctezuma de la Barrera
8,790,351 B2 7/2014 Paradis et al.
(Continued)

FOREIGN PATENT DOCUMENTS

WO 2012100825 A1 8/2012
WO 2015120892 A2 8/2015

OTHER PUBLICATIONS

European Office Action for European Patent Application No. 15729363.0 dated Apr. 29, 2020.
(Continued)

*Primary Examiner* — Pinalben Patel
(74) *Attorney, Agent, or Firm* — DLA Piper LLP

(57) ABSTRACT

The present invention relates to a method for registering a first anatomical structure (1) which is articulately coupled to a second anatomical structure (2), the method being constituted to be executed by a computer and comprising the steps of:
acquiring second structure correlation data describing the spatial position of at least one correlation feature (3) relative to the second anatomical structure (2):
acquiring coupling data describing a positional fixation (6) of the first anatomical structure (1) relative to the second anatomical structure (2), which is set by the articulated coupling (4) between the first anatomical structure (1) and the second anatomical structure (2);
determining, based on the second structure correlation data and the coupling data, first structure correlation data describing the spatial position of the at least one correlation feature (3) relative to the first anatomical structure (1).

(Continued)

Figure 1:
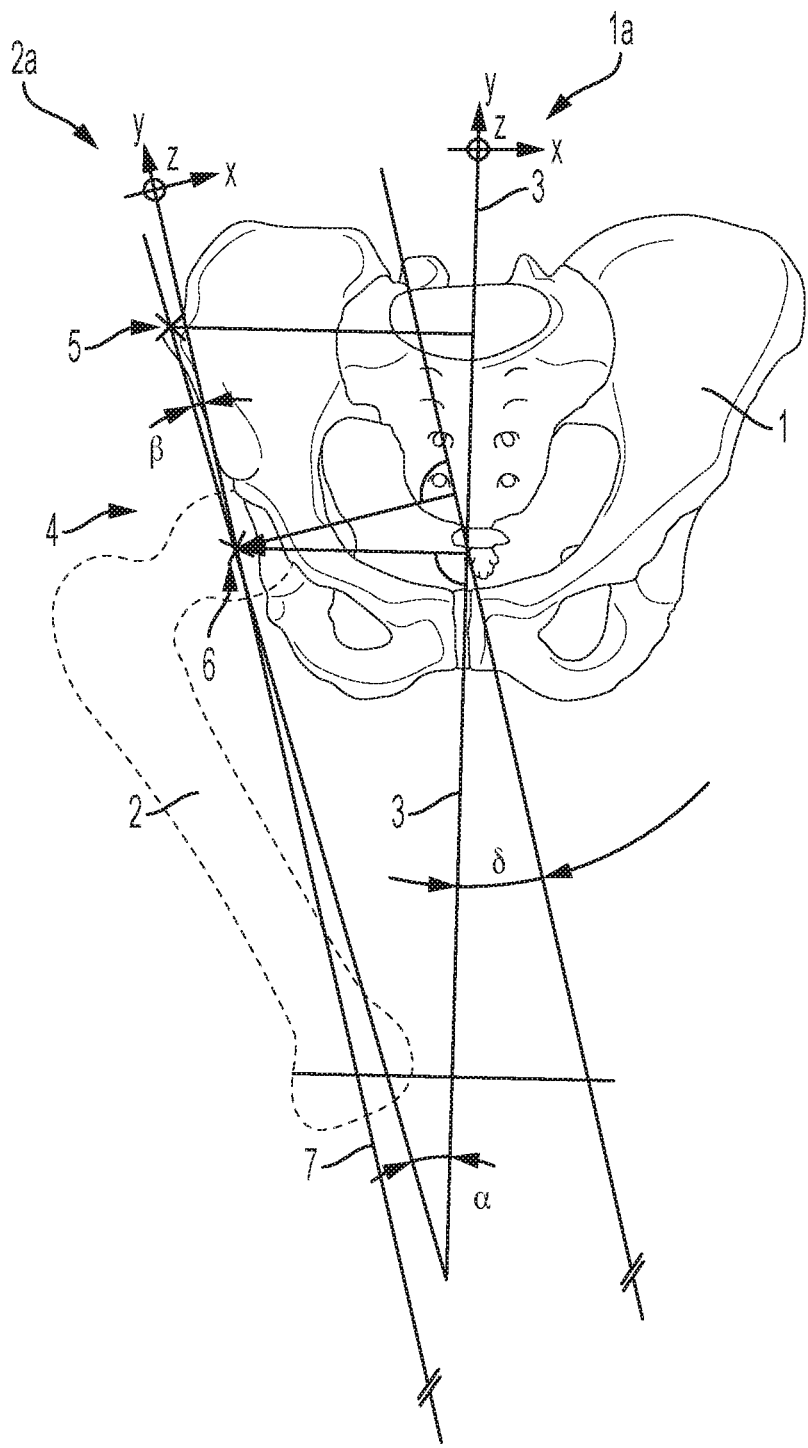

The present invention further relates to a corresponding computer program and system.

18 Claims, 2 Drawing Sheets

(51) Int. Cl.
    *A61B 34/10*     (2016.01)
    *G06T 7/32*     (2017.01)
    *G06T 7/33*     (2017.01)
    *A61B 90/00*     (2016.01)
    *A61B 5/11*     (2006.01)

(52) U.S. Cl.
    CPC ............. *G06T 7/73* (2017.01); *G06T 7/74* (2017.01); *A61B 5/1121* (2013.01); *A61B 2034/105* (2016.02); *A61B 2034/2065* (2016.02); *A61B 2034/2072* (2016.02); *A61B 2090/364* (2016.02); *A61B 2090/376* (2016.02); *G06T 2207/10116* (2013.01); *G06T 2207/30008* (2013.01); *G06T 2207/30204* (2013.01)

(58) Field of Classification Search
    CPC ........... A61B 2034/2072; A61B 34/20; A61B 2034/2065; G06T 7/32; G06T 2207/10116; G06T 7/73; G06T 7/337; G06T 2207/30008; G06T 7/74; G06T 2207/30204
    See application file for complete search history.

(56) References Cited

U.S. PATENT DOCUMENTS

| | | | |
|---|---|---|---|
| 11,172,995 B2 * | 11/2021 | Dohmen | G06T 7/73 |
| 2004/0167390 A1 * | 8/2004 | Alexander | A61B 5/055 600/410 |
| 2004/0199232 A1 | 10/2004 | Wallace et al. | |
| 2005/0245820 A1 | 11/2005 | Sarin | |
| 2006/0004284 A1 | 1/2006 | Grunschlager et al. | |
| 2006/0122541 A1 * | 6/2006 | Tuma | A61B 5/4528 600/587 |
| 2007/0015995 A1 * | 1/2007 | Lang | A61B 5/055 600/407 |
| 2008/0137931 A1 | 6/2008 | Drumm et al. | |
| 2012/0014559 A1 | 1/2012 | Suehling et al. | |
| 2014/0052149 A1 | 2/2014 | van der Walt et al. | |
| 2014/0094694 A1 | 4/2014 | Moctezuma de la Barrera | |
| 2014/0303493 A1 | 10/2014 | Kawasaki et al. | |

OTHER PUBLICATIONS

European Patent Office, International Search Report and Written Opinion for Application No. PCT/EP2015/062008 dated Dec. 2, 2016.

Barratt et al., "Instantiation and Registration of Statistical Shape Models of the Femur and Pelvis Using 3D Ultrasound Imaging," 2008, Medical Image Analysis 12(3):358-374.

Sugano et al., "Accuracy Evaluation of Surface-Based Registration Methods in a Computer Navigation System for Hip Surgery Performed Through a Posterolateral Approach," 2001, Computer Aided Surgery 6(4):195-203.

* cited by examiner

METHOD FOR REGISTERING ARTICULATED ANATOMICAL STRUCTURES

RELATED APPLICATIONS

This application is a continuation of U.S. application Ser. No. 15/576,172, filed Nov. 21, 2017, titled METHOD FOR REGISTERING ARTICULATED ANATOMICAL STRUCTURES, which is a national phase application of International Application No. PCT/EP2015/062008, filed on May 29, 2015, titled METHOD FOR REGISTERING ARTICULATED ANATOMICAL STRUCTURES the contents of each of which are incorporated herein by reference in their entirety.

The present invention relates to a data processing method, performed by a computer, for registering articulated anatomical structures and to a corresponding computer program and system.

Image-guided surgery (IGS) has become more and more important for a wide range of medical procedures. For these medical procedures, it is desirable to know the position of a specific anatomical structure in a medical image of the patient's body who is to be treated. Further it is desirable to know the exact location of medical items such as instruments or implants relative to anatomical structures. For example, medical personnel wishes to associate a visually identified part of the real body within a specific image feature representing that part of the real body in order to determine the location on the specific patient's body at which the envisaged medical procedure is to be carried out.

For this purpose, a registration procedure has to be carried out to initially allocate the position of a specific anatomical structure in real space to a position of an image of the anatomical structure in a (virtual) image space and/or to medical items. Common registration procedures involve palpating landmarks of the anatomical structure so as to acquire their spatial position within the surgical environment. For example, the US 2012/100825 A1 teaches to palpate certain reference features of a pelvic bone with a pointer instrument which is tracked by a medical tracking system, wherein a navigation system then saves and stores the spatial position and orientation of the palpated reference features for further processing during surgery.

Palpating crucial landmarks is however often compromised by external circumstances, such as the positioning of the patient or the range of the sterile operating field within which landmarks can be palpated. For example, palpating all necessary pelvis landmarks of a patient lying in a lateral position is rather difficult, since landmarks lying either on the left or the right side of the patient cannot be reached properly.

The present invention provides a method, a computer program and a system which enable the registration of an anatomical patient structure such as a bone even if some crucial landmarks for registering the anatomical structure cannot be reached for registration.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

According to the present invention, a method for registering a first anatomical structure which is articulately coupled to a second anatomical structure is provided, wherein the method is constituted to be executed by a computer and comprises the steps of:
acquiring second structure correlation data describing the spatial position of at least one correlation feature relative to the second anatomical structure;
acquiring coupling data describing a positional fixation of the first anatomical structure relative to the second anatomical structure, which is set by the articulated coupling between the first anatomical structure and the second anatomical structure;
determining, based on the second structure correlation data and the coupling data, first structure correlation data describing the spatial position of the at least one correlation feature relative to the first anatomical structure.

In other words, the inventive registration method utilizes additional data different from the positional data of landmarks on the anatomical structure to be registered. Specifically, the inventive method uses data provided by a further anatomical structure that is connected in a joint to the structure to be registered. The structures connected to each other in that joint are substantially rigid structures, for example structures comprising bone and/or cartilage-tissue. The articulated coupling between both structures can comprise any conceivable anatomical joint, such as a ball joint plane joint, saddle joint, pivot joint, hinge joint or ellipsoid joint, providing at least one and up to three rotational and/or translational degrees of freedom, but also a positional fixation between the anatomical structures. Specific examples for such joints are a human hip joint or shoulder joint, a human knee joint or elbow joint. However, any articulated coupling between two substantially rigid anatomical structures can be considered.

The present invention utilizes the fact that at an articulated coupling between two rigid structures defines certain geometrical conditions for both of the structures coupled to each other via said coupling. For example, the centre of rotation of a ball joint having three degrees of freedom, or the rotational axis of a hinge joint having one degree of freedom will always maintain its spatial position with respect to both of the anatomical structures. The present invention has realized that this can be used to "transfer" registration data from one anatomical structure to the other anatomical structure coupled thereto via the joint.

Further, a predefined spatial correlation with respect to one of the anatomical structures can be transferred to a corresponding spatial correlation with respect to the other anatomical structure. For example, the known spatial position (spatial location and/or spatial alignment) of an anatomical direction or plane with respect to one of the anatomical structures can be used to calculate the spatial position of the anatomical direction or plane with respect to the other anatomical structure, even though the other anatomical structure has not been (fully) registered.

Determining the first structure correlation data may involve defining a first coordinate system positionally assigned to the first anatomical structure and a second coordinate system positionally assigned to the second anatomical structure; and at least one reference feature for which the spatial position relative to the positional fixation is determined within the first coordinate system and for which the spatial position is determined within the second coordinate system;
and wherein the spatial position of the at least correlation feature relative to the first anatomical structure is determined based on establishing within the second coordinate system the spatial position of the at least one reference feature relative to the positional fixation, that has been determined within the first coordinate system.

With coordinate systems, particularly Cartesian coordinate systems (CCS) defined for both of the anatomical structures, the correlation data can be transferred fast and easily from one coordinate system to the other coordinate system. Further, the inventive method may consider the spatial position of one or more reference features relative to the positional fixation between the anatomical structures. Such reference features which may be constituted by landmarks of one of the anatomical structures help in establishing a transformation from one coordinate system to the other coordinate system. In case the spatial position of the reference features relative to the positional fixation between the anatomical structures is equal in both coordinate systems, it can be assumed that both coordinate systems are aligned with each other, i.e. the anatomical directions are equal in both coordinate systems.

Since the reference features are constituted by landmarks of one of the anatomical structures the relative position between the at least one reference feature and the positional fixation such as the centre of rotation or rotational axis of the joint is invariant in the coordinate system assigned to the respective anatomical structures. This means that the spatial orientation of the other coordinate system can be altered with respect to the first coordinate system so that the spatial position of the at least one reference feature within the other coordinate system and relative to the positional fixation of the joint is consequently also altered. Therefore, it is possible to "align" the two coordinate systems by establishing the same relative position between the at least one reference feature and the positional fixation.

Moreover, acquiring the second structure correlation data may comprise determining the spatial position of the at least one geometrical feature of the second anatomical structure, and defining the spatial position of the at least one correlation feature relative to the at least one geometrical feature. In other words, the at least one correlation feature may be defined relative to geometrical features of the second anatomical structure, the position of which can be easily identified, for example within an image of the second anatomical structure or from a registration of the second anatomical structure.

It is also possible to determine the position and/or positional relationship of any feature, particularly the positional fixation, at least one correlation feature and/or at least one reference feature, from at least one image taken of at least one of the first anatomical structure and the second anatomical structure.

More particularly, the at least one image taken from the first and/or from the second anatomical structure may be an x-ray-image, that may have been taken in an anterior-posterior direction of the patient.

Such image allows for determining the position and/or positional relationship of at least one of those features via direct measurements within the image. For example, the distance between two features and/or an angle between two features may be measured within an image, wherein such measurements may serve as a basis for establishing the same positional relationship in both of the coordinate systems as already explained further above.

In order to establish the same spatial relationship between the at least one reference feature and the positional fixation, the spatial position of the second anatomical structure together with the second coordinate system assigned thereto may be altered relative to the first anatomical structure and the first coordinate system assigned thereto, wherein the limits of the positional fixation set by the articulated coupling are considered.

For this purpose, a computational algorithm may be used, which may "virtually" alter the position of the second anatomical structure/second coordinate system relative to the first anatomical structure/first coordinate system within the limits defined by the joint.

The inventive method may be used for pelvis registration, wherein data of a femur-registration is used to register the pelvis. In this example, the pelvis constitutes the first anatomical structure, the femur constitutes the second anatomical structure, the midsagittal plane constitutes a correlation feature, a mechanical axis of the femur constitutes the geometrical feature, an anatomical landmark of the pelvis, such as an anterior superior iliac spine or a most lateral point of the iliac crest may constitute a reference feature and/or a centre of rotation of a hip joint constitutes a positional fixation.

Although any anatomical landmark may serve as a reference feature, prominent or at least distinctive landmarks are preferred, as they can be easily identified on the patient later on. It is also conceivable that at least one reference feature lying on the midsagittal plane of the patient is chosen, which means that this reference feature need not be identified on an image, for example on an x-ray-image of the patient, as its distance from the midsagittal plane is by definition 0. In this case, only the distance of the centre of rotation relative to the midsagittal plane has to be determined.

For this specific example of the inventive method, the midsagittal plane may be defined within the second coordinate system as being parallel to the mechanical axis of the femur, which by definition runs through the centre of rotation of the hip joint. Moreover, the midsagittal plane can be defined as being spaced from this mechanical axis in a medial direction by a distance which is equal to the distance between the centre of rotation of the hip joint and the midsagittal plane within the first coordinate system. Since the position of the hip joint is invariant in both coordinate systems assigned to the first anatomical structure and to the second anatomical structure, respectively, the distance between the midsagittal plane and the centre of rotation of the hip joint is also equal for both coordinate systems.

Since a neutral position of the femur is by definition a state for which the mechanical axis of the femur is located parallel to the midsagittal plane of the pelvis, the spatial position of the midsagittal plane within the coordinate system assigned to the pelvis can be derived from the spatial position of the femur's mechanical axis within the coordinate system assigned to the femur, provided that the distance between the midsagittal plane and the centre of rotation of the hip joint is known and both coordinate systems are aligned to each other, which can be done by establishing the same spatial relationship of the at least one reference feature relative to the joint's centre of rotation.

Assuming that the spatial position of the at least one correlation feature is transferred from one coordinate system to another coordinate system based on a two-dimensional image, such as an x-ray-image, at least one degree of freedom remains for the correlation feature's position within the coordinate system it is transferred to. This can be compensated for by defining at least one spatial direction in the initial coordinate system, which may be done by acquiring at least one further feature or landmark of the first anatomical structure. Alternatively or additionally, it is also possible to determine the spatial position of at least one landmark of the first anatomical structure, which provides further data to determine the spatial position of the correlation feature (for example the midsagittal plane) within the first coordinate system. Further, it is conceivable to use further data taken from an anatomical atlas describing the first anatomical structure of the patient, or to acquire further images which may be also taken from different directions. From this additional data anatomical directions within the first coordinate system can be derived.

A further aspect of the present invention relates to a corresponding computer program which, when running on a computer, causes the computer to perform the method steps of acquiring second structure correlation data describing the spatial position of at least one correlation feature relative to the second anatomical structure; acquiring coupling data describing a positional fixation of the first anatomical structure relative to the second anatomical structure, which is set by the articulated coupling between the first anatomical structure and the second anatomical structure; determining, based on the second structure correlation data and the coupling data, first structure correlation data describing the spatial position of the at least one correlation feature relative to the first anatomical structure. A further aspect of the invention relates to a corresponding program storage medium on which the program is stored, in particular in a non-transitory form, wherein this method may comprise any of the features described herein.

A further aspect of the present invention relates to a corresponding system for registering a first anatomical structure, which comprises a computer with a program storage medium on which such program is stored.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google. Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The n-dimensional image of a body is registered when the spatial location of each point of an actual object within a space, for example a body part in an operating theatre, is assigned an image data point of an image (CT, MR, etc.) stored in a navigation system.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:
the computer of the preceding claim, for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the data processing method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

Preferably, atlas data is acquired which describes (for example defines, more particularly represents and/or is) a general three-dimensional shape of the anatomical body part. The atlas data therefore represents an atlas of the anatomical body part. An anatomical atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. For this reason alone, no surgical or therapeutic activity and in particular no surgical or therapeutic step is necessitated or implied by carrying out the invention.

The present invention may be implemented into the "Trauma CAD"—system, an X-ray planning software of Brainlab AG, Germany.

In the following, the invention is described with reference to the enclosed figures which represent preferred embodiments of the invention. The scope of the invention is however not limited to the specific features disclosed in the figures, which show:

FIG. 1 schematically shows the geometrical consideration underlying the present invention for a pelvis-femur-registration.

Figure 2:
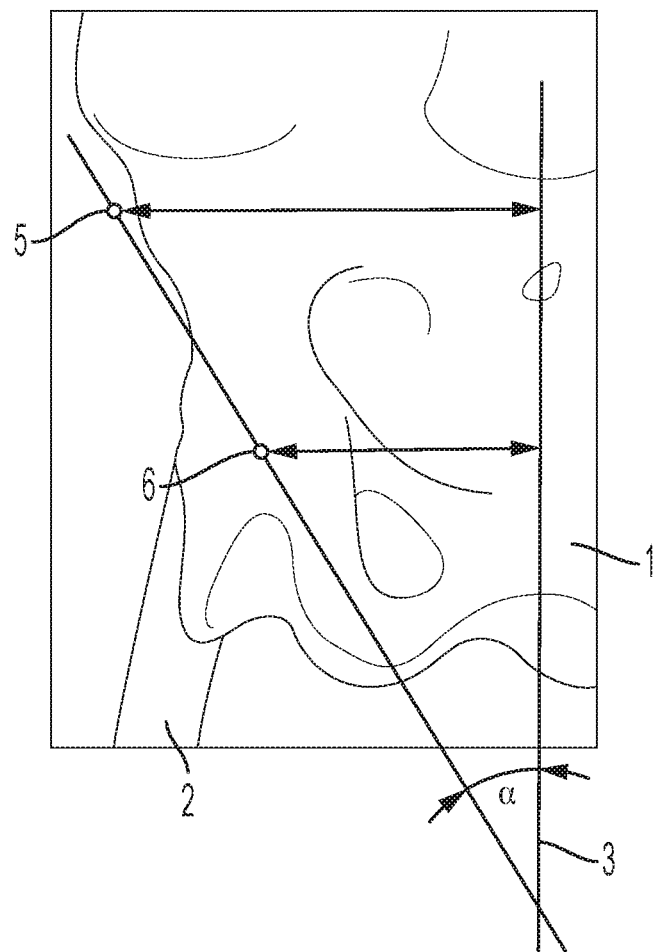

FIG. 2 shows a two-dimensional X-ray-image partially depicting a human pelvis and a human femur FIG. 1 shows a human pelvis 1 to which a human femur 2 (shown in broken lines) is coupled via a hip joint 4 having a centre of rotation 6.

In case the pelvis 1 cannot be sufficiently registered, for example when the patient is lying in a lateral position, the inventive idea is to use data obtained by the registration of the femur 2, for the registration of the pelvis 1. For this purpose, the inventive method considers the fact that the position of the centre of rotations 6 of the hip joint 4 is invariant with respect to both, the pelvis 1 and the femur 2, even though the spatial position of the femur 2 can be altered relative to the pelvis 1 within the limits defined by the hip joint 4.

According to the present invention, the spatial position of the midsagittal plane 3 with respect to the pelvis 1 can be obtained as follows:

First of all, coordinate systems 1a and 2a are assigned to the pelvis 1 and to the femur 2, respectively. For example, the coordinate system 2a may be defined to have an y-axis being parallel to the mechanical axis 7 of the femur, wherein the x-axis of the coordinate system 2a may be defined as a direction being perpendicular to the y-axis and parallel to the medial-lateral-direction with respect to the femur 2. Both, the x-axis and the y-axis of the femur-coordinate system 2a can be obtained by a (full) registration of the femur 2, which is widely known in the prior art.

Further, a two-dimensional x-ray-image is taken in an anterior-posterior direction from the pelvis 1 and the femur 2, which allows to define within the image the spatial position of the midsagittal plane 3 relative to the pelvis 1, as this is shown in FIG. 2. Moreover, the spatial positions of the centre of rotation 6 and of the anterior superior iliac spine 5 serving as a reference point are determined within the image, wherein the spatial relationship between the reference point 5 and the centre of rotation 6 is also determined. This can be done by either measuring, for example in a medial-lateral direction, the distance of the points 5 and 6 relative to the midsagittal plane 3, or by determining the angle α drawn within the image plane by the midsagittal plane 1 and the straight including points 5 and 6.

The (full) registration of the femur 2 further provides the spatial position of the mechanical axis of the femur 2, which runs through the centre of rotation 6.

Since the spatial alignment of the midsagittal plane 3 within the coordinate system 2a of the femur 2 is by definition parallel to the mechanical axis 7 of the femur 2, and the distance between the mechanical axis 7 and the midsagittal plane 3 in a medial direction is known to be equal to the distance between the centre of rotation 6 and the midsagittal plane 3 measured in the x-ray-image, the spatial position (spatial location and spatial alignment) of the midsagittal plane 3 within the coordinate system 2a can be calculated.

In order to determine the midsagittal plane 3 within the coordinate system 1a assigned to the femur 1, the coordinate system 2a has to be aligned with coordinate system 1a.

For this purpose, the relative position between the anterior superior iliac spine 5 and the centre of rotation 6 within the coordinate system 2a is adjusted to the corresponding and invariant spatial relationship within coordinate system 1a by virtually rotating the femur 2 together with coordinate system 2a around the centre of rotation 6. In the case shown in FIG. 1, the same spatial relationship between the anterior superior iliac spine 5 and the centre of rotation 6 will be reached by rotating the femur 2 around the centre of rotation 6 in a clockwise direction by an angle γ. As a result, the angle α drawn between the midsagittal plane 3 and the straight including the anterior superior iliac spine 5 and the centre of rotation 6 within the coordinate system 1a is equal to the angle β drawn between the midsagittal plane 3 or the mechanical axis 7 and the straight including the anterior iliac spine 5 and the centre of rotation 6 within coordinate system 2a.

As a result, the spatial position of the midsagittal plane 3 within the coordinate system 1a of the pelvis 1 can be calculated from the registration of the femur 2 and the spatial position of the anterior superior iliac spine 5 of the pelvis 1. It also becomes apparent from FIG. 1 that the information obtained as to the spatial position of the midsagittal plane 3 with respect to the pelvis 1 can be used later on for a patient registration in situ. For such registration it is not necessary to approach reference points on both sides of the pelvis 1, which is especially beneficial with a patient lying in a lateral position.

The invention claimed is:

1. A computer implemented method for providing surgical guidance information, the method comprising:
    assigning first and second coordinate systems to a pelvis of a patient and a femur of the patient, respectively, wherein the femur is registered in the second coordinate system to thereby provide a first spatial position of a mechanical axis of the femur in the second coordinate system;
    defining within an obtained image of the patient a second spatial position of a midsagittal plane relative to the pelvis and determining within the image a spatial relationship of a centre of rotation of a hip joint of the patient and a reference feature, wherein the midsagittal plane is parallel to the mechanical axis of the femur;
    registering the pelvis in the first coordinate system comprising determining a third spatial position of the midsagittal plane within the first coordinate system by aligning the second coordinate system with the first coordinate system comprising adjusting the relative position of the reference feature and the centre of rotation within the second coordinate system based on the determined spatial relationship; and
    generating and outputting surgical guidance information to an indicating device based on the registration and the second spatial position of the midsagittal plane relative to the pelvis.

2. The method according to claim 1, further comprising virtually rotating the femur together with the second coordinate system around the centre of rotation of the hip joint to achieve the alignment.

3. The method according to claim 1, wherein the second coordinate system is defined to have a y-axis parallel to the mechanical axis of the femur and an x-axis of the second coordinate system is perpendicular to the y-axis and parallel to a medial-lateral-direction with respect to the femur.

4. The method according to claim 1, wherein the image comprises a two-dimensional x-ray image taken in an anterior-posterior direction from the pelvis and the femur.

5. The method according to claim 1, wherein the reference feature comprises an anterior superior iliac spine of the pelvis.

6. The method according to claim 1, further comprising measuring in a medial-lateral direction a distance of the reference point and the centre of rotation of the hip joint relative to the midsagittal plane, or determining an angle within a plane of the image defined by the midsagittal plane and a straight comprising the reference point and the centre of rotation of the hip joint, to determine the spatial relationship.

7. A computing device, comprising memory comprising programmed instructions stored thereon for providing surgical guidance information and one or more processors coupled to the memory and configured to execute the stored programmed instructions to:
    assign first and second coordinate systems to a pelvis of a patient and a femur of the patient, respectively, wherein the femur is registered in the second coordinate system to thereby provide a first spatial position of a mechanical axis of the femur in the second coordinate system;
    define within an obtained image of the patient a second spatial position of a midsagittal plane relative to the pelvis and determine within the image a spatial relationship of a centre of rotation of a hip joint of the patient and a reference feature, wherein the midsagittal plane is parallel to the mechanical axis of the femur;
    register the pelvis in the first coordinate system comprising determining a third spatial position of the midsagittal plane within the first coordinate system by aligning the second coordinate system with the first coordinate system comprising adjusting the relative position of the reference feature and the centre of rotation within the second coordinate system based on the determined spatial relationship; and
    generate and output surgical guidance information to an indicating device based on the registration and the second spatial position of the midsagittal plane relative to the pelvis.

8. The computing device of claim 7, wherein the one or more processors are further configured to execute the stored programmed instructions to virtually rotate the femur together with the second coordinate system around the centre of rotation of the hip joint to achieve the alignment.

9. The computing device of claim 7, wherein the second coordinate system is defined to have a y-axis parallel to the mechanical axis of the femur and an x-axis of the second coordinate system is perpendicular to the y-axis and parallel to a medial-lateral-direction with respect to the femur.

10. The computing device of claim 7, wherein the image comprises a two-dimensional x-ray image taken in an anterior-posterior direction from the pelvis and the femur.

11. The computing device of claim 7, wherein the reference feature comprises an anterior superior iliac spine of the pelvis.

12. The computing device of claim 7, wherein the one or more processors are further configured to execute the stored programmed instructions to measure in a medial-lateral direction a distance of the reference point and the centre of rotation of the hip joint relative to the midsagittal plane, or determine an angle within a plane of the image defined by the midsagittal plane and a straight comprising the reference point and the centre of rotation of the hip joint, to determine the spatial relationship.

13. A non-transitory computer readable medium having stored thereon instructions for providing surgical guidance information comprising executable code that, when executed by one or more processors, causes the processors to:
assign first and second coordinate systems to a pelvis of a patient and a femur of the patient, respectively, wherein the femur is registered in the second coordinate system to thereby provide a first spatial position of a mechanical axis of the femur in the second coordinate system;
define within an obtained image of the patient a second spatial position of a midsagittal plane relative to the pelvis and determine within the image a spatial relationship of a centre of rotation of a hip joint of the patient and a reference feature, wherein the midsagittal plane is parallel to the mechanical axis of the femur;
register the pelvis in the first coordinate system comprising determining a third spatial position of the midsagittal plane within the first coordinate system by aligning the second coordinate system with the first coordinate system comprising adjusting the relative position of the reference feature and the centre of rotation within the second coordinate system based on the determined spatial relationship; and
generate and output surgical guidance information to an indicating device based on the registration and the second spatial position of the midsagittal plane relative to the pelvis.

14. The non-transitory computer readable medium of claim 13, wherein the executable code, when executed by the processors, further causes the processors to virtually rotate the femur together with the second coordinate system around the centre of rotation of the hip joint to achieve the alignment.

15. The non-transitory computer readable medium of claim 13, wherein the second coordinate system is defined to have a y-axis parallel to the mechanical axis of the femur and an x-axis of the second coordinate system is perpendicular to the y-axis and parallel to a medial-lateral-direction with respect to the femur.

16. The non-transitory computer readable medium of claim 13, wherein the image comprises a two-dimensional x-ray image taken in an anterior-posterior direction from the pelvis and the femur.

17. The non-transitory computer readable medium of claim 13, wherein the reference feature comprises an anterior superior iliac spine of the pelvis.

18. The non-transitory computer readable medium of claim 13, wherein the executable code, when executed by the processors, further causes the processors to measure in a medial-lateral direction a distance of the reference point and the centre of rotation of the hip joint relative to the midsagittal plane, or determine an angle within a plane of the image defined by the midsagittal plane and a straight comprising the reference point and the centre of rotation of the hip joint, to determine the spatial relationship.

* * * * *